United States Patent [19]
Murotani et al.

[11] Patent Number: 5,594,146
[45] Date of Patent: Jan. 14, 1997

[54] PROCESS FOR PRODUCING 5-AMINOTETRAZOLE

[75] Inventors: Masahiro Murotani, Toyama; Hajime Mura, Uozu; Makoto Takeda, Takaoka; Hiroshi Shibafuchi, Uozu, all of Japan

[73] Assignee: Nippon Carbide Kogyo Kabushiki Kaisha, Tokyo, Japan

[21] Appl. No.: 392,308

[22] Filed: Feb. 22, 1995

[30]    Foreign Application Priority Data

Feb. 24, 1994 [JP] Japan .................................. 6-049930

[51] Int. Cl.$^6$ ................................................. C07D 257/06
[52] U.S. Cl. ............................................................. 548/251
[58] Field of Search ............................................... 548/251

[56]                References Cited

U.S. PATENT DOCUMENTS 4,906,778  5/1990  Schaffhausen ........................ 564/227

FOREIGN PATENT DOCUMENTS 190055   9/1981  Czechoslovakia .
536916   8/1993  European Pat. Off. .
50-5175  2/1975  Japan .
5-117070 5/1993  Japan .

OTHER PUBLICATIONS

J. Org. Chem., 15, 1082, (1950), "Synthesis of 5–AT from the reaction of cyanamide and hydrogen azide acid".

J. Org. Chem., 18, 779, (1953), "Synthesis of 5–AT from salts of diazoguanidine, which is prepared from aminoguanidine salt and nitrous acid".

The Journal of Organic Chemistry, vol. 18, Jul. 1953, pp. 779–790, William G. Finnegan et al.

Chemical Abstracts, vol. 96., No. 11, 15 Mar. 1982, abstract No. 85565t, p. 593 & CS-A-190 055 (Arient Josef et al.).

*Primary Examiner*—David B. Springer
*Attorney, Agent, or Firm*—Pennie & Edmonds

[57]                ABSTRACT

A process for producing 5-aminotetrazole comprising the steps of: reacting cyanamide with hydrazine in a solvent to form a salt of aminoguanidine; adding thereto an acid and then a nitrite to form a salt of diazoguanidine; and cyclizing the salt of diazoguanidine, upon heating, to thereby produce the 5-aminotetrazole, without isolating the intermediate product and also a process for producing 5-aminotetrazole or a metal salt thereof in the form of powder by spray drying.

5 Claims, 4 Drawing Sheets

Fig. 1

PROCESS FOR PRODUCING 5-AMINOTETRAZOLE

BACKGROUND OF THE INVENTION

1. Field of the Invention

The present invention relates to a process for commercially producing 5-aminotetrazole suitable for use as an intermediate in the production of gas generants, medicines or pesticides. More specifically, it relates to a process for producing 5-aminotetrazole from cyanamide and hydrazine. The present invention also relates to a method for powdering the 5-aminotetrazole or a metal salt thereof by spray drying.

2. Description of the Related Art

Several processes for producing 5-aminotetrazole are already known in the art. For example, Journal of Organic Chemistry, 15, 1082 (1950) proposes a process for producing 5-aminotetrazole by reacting cyanamide with hydrazoic acid to obtain imidoazide, followed by cyclization or ring formation thereof. This reaction is considered to proceed as follows.

In addition, Journal of Organic Chemistry, 18, 779 (1953) proposes a process for producing 5-substituted tetrazole by reacting a salt of aminoguanidine with nitrite to form a salt of diazoguanidine, followed by cyclization thereof with sodium acetate, sodium carbonate or diluted mineral acid upon heating, as follows. Furthermore, Czechoslovakia Patent No. 190055 (patented Sep. 15, 1981) proposes a process for producing 5-aminotetrazole by reacting aminoguanidine sulfate with nitrite in HCl to form diazoguanidinium chloride, followed by cyclization with sodium acetate upon heating.

wherein X represents I, $HSO_4$ or Cl.

However, since the hydrazoic acid, which is explosive and deadly poisonous, must handle as a starting material in the form of a free acid in the above-mentioned first proposal, special attentions should be paid to materials and sealability of apparatuses, and facilities for treating exhaust gas and waste water, and therefore, this proposal was difficult to be practically used as an industrial scale.

Even in the above-mentioned second proposal, it is necessary to use an expensive salt of aminoguanidine as a starting material. Furthermore, a salt of diazoguanidine, which should be isolated as an intermedial product, is an unstable compound, and therefore, a portion thereof is decomposed to decrease the yield and also the use of the special materials for the apparatuses or the special facilities for the treatment apparatuses etc. Thus, again, this proposal is difficult to be practiced at an industrial scale and is not economical.

On the other hand, the materials capable of forming a salt with a reaction of 5-aminotetrazole include mineral acids, alkali metals, alkaline earth metals, and transition metals. Typical examples of the mineral acids are hydrochloric acid, sulfuric acid, nitric acid, phosphoric acid, etc. The alkali metals and alkaline earth metals are mainly used as the hydroxides or oxides for the reaction, typically in the form of sodium hydroxide, potassium hydroxide, magnesium oxide, etc. Typical examples of the transition metals are nickel, zinc, copper, molybdenum, iron, etc. These transition metals are not usually used in the form of the metal per se, but used as the inorganic metal salts or organic metal salts. Examples of the inorganic metal salts are copper chloride and molybdenum chloride, etc. and examples of the organic metal salts are nickel acetate and zinc acetate.

Especially many metal salts of 5-aminotetrazole have high solubilities in water and the other organic solvents. Accordingly, when anhydrous or water-free salts of 5-aminotetrazole are intended to obtain by concentrating the solution containing the above-mentioned metal salts of 5-aminotetrazole, followed by crystallizing, separating and drying the resultant crystals. However, since the solubilities thereof in the solvent are high, there are many cases that the yield of the desired anhydrous salt during the separation step of the crystalline is low and the filtering properties are poor. Furthermore, due to the inherent properties of the materials there are many cases where the hydration is easy to occur. Thus, the drying step thereafter should be sufficiently effected. As mentioned above, the steps of the prior art processes are totally troublesome, and therefore, there are needs that the desired anhydride products can be easily obtained by simply separating and drying the resultant products.

It is considered that the reaction mixture containing the desired metal salts of 5-aminotetrazole is dispersed and crystallized in an organic solvent. However, the use of organic solvents is not preferable from the viewpoints of operation as well as safety and sanitation. In addition, when the organic solvent is recovered, since the new process step is added for this purpose, the production cost is increased.

Azide based conventional gas generants using, for example, sodium azide as a fuel have the problem of the toxicity of the unreacted azide remained. In addition, in the conventional gas generation apparatus, the reaction products formed simultaneously with the generation of gas should be efficiently filtered with a filter.

On the other hand, since conventional non-azide based gas generants are intended to utilize due to their low toxicity, there are disadvantages that the combustion temperature becomes higher, when compared with the case of the azide-based gas generants, and therefore, the combustion temperature is higher than the melting point of the remaining reaction products are difficult to separate by a filter. Therefore, it is intended to modify the form of the reaction products by the addition of an appropriate additive such that the filtration can be effected. It is believed that, to obtain the particles of the reaction product capable of being easily filtered, a high melting point component and an appropriate low boiling point component are coexisted and the high melting point component is fusion coagulated with the low boiling point to thereby form the particles.

The alkali metal salts of 5-aminotetrazole can be a nitrogen gas generating source as a fuel and also can form an appropriate low boiling point component by the reaction with other additives such as silicates or carbonates. Furthermore, the alkali metal salts of 5-aminotetrazole has an effect that the amount of nitrogen oxides ($NO_x$) generated during the decomposition can be reduced.

SUMMARY OF THE INVENTION

Accordingly, the objects of the present invention are to eliminate the above-mentioned problems of the prior art and to provide a process for commercially producing 5-aminotetrazole with safety at a cheaper cost.

Another object of the present invention is to provide a process for producing an anhydrous (or water-free) 5-aminotetrazole (or a metal salt thereof) at a high yield in the form of powder (or particles) which are capable of being easily handled.

Other objects and advantages of the present invention will be apparent from the following description.

In accordance with the present invention, there is provided a process for producing 5-aminotetrazole comprising the steps of:

(a) reacting cyanamide with hydrazine in a solvent to form a salt of aminoguanidine;

(b) adding thereto an acid and then a nitrite to form a salt of diazoguanidine; and (c) cyclizing the salt of diazoguanidine, upon heating, to thereby produce the 5-aminotetrazole, without isolating the intermediate product.

In accordance with the present invention, there is also provided a process for producing 5-aminotetrazole in the form of powder (or particles) comprising spray drying a solution of the 5-aminotetrazole obtained above or a metal salt thereof. Especially, the water-soluble metal salts (e.g., potassium salt, magnesium salt, etc.) can be suitably powdered according to this process.

BRIEF DESCRIPTION OF THE DRAWINGS

The present invention will be better understood from the description set forth below with reference to the accompanying drawings, wherein.

DESCRIPTION OF THE PREFERRED EMBODIMENTS

The present invention will now be described in more detail.

According to the present invention, the desired 5-aminotetrazole and the salts thereof can be easily produced, with safety, by forming aminoguanidine from cyanamide and hydrazine, then forming a salt of diazoguanidine by the reaction with nitrite, followed by cyclizing or ring forming, without isolating the salt of diazoguanidine.

The reaction schemes according to the present invention can be summarized as follows.

$H_2NCN + H_2NNH_2 \cdot HX \longrightarrow H_2NCNHNH_2 \cdot HX \longrightarrow$ wherein X represents Cl, $HSO_4$, $NO_3$, $H_2PO_4$, etc.

According to the present invention, cyanamide is first allowed to react with hydrazine in an appropriate solvent (e.g., water, ethanol, isopropanol, etc.) to form a solution of a salt of aminoguanidine. This reaction an acid is added to the hydrazine or hydrazine hydrate in the solvent to thereby adjust the pH of the solution to prepare the solution or slurry of a salt of hydrazine. It is preferable in this reaction that about 0.5 to 3 equivalent, more preferably about 0.8 to 1.2 equivalent, based upon 1 mole of the hydrazine hydrate. Alternatively, the solution of a salt of hydrazine can be prepared by dissolving the salt of hydrazine in an appropriate solvent.

The acids usable for neutralizing the hydrazine hydrate are not specifically limited and preferably include, for example, hydrochloric acid, sulfuric acid, nitric acid, carboxylic acid, and phosphoric acid. From the economical viewpoints, the use of hydrochloric acid or sulfuric acid is most preferable. Examples of the salts of hydrazine usable in the present invention are hydrochloride, sulfate, nitrate and carbonate. From the economical viewpoints, the use of hydrochloride and sulfate is most preferable.

In the present invention, the cyanamide preferable in an amount of about 0.8 to 3 mole, more preferably 0.8 to 1.5 mole, based upon 1 mole of hydrazine, is added to the above-mentioned solution of the salt of hydrazine, followed by heating to form a solution of a salt of aminoguanidine.

The cyanamide to be used in the present reaction can be added either in the form of a crystalline or a solution. When the cyanamide is added in the form of a solution, any solvent which does not react with the starting materials and the reaction intermediates and which is capable of dissolving the starting materials can be used without any limitation. Among such solvents, the use of water is most preferable from the viewpoints of the cheap cost and the high safety. The preferable concentration of cyanamide is about 5 to 100% by weight, more preferably 10 to 60% by weight.

Although there are no specific limitations to the reaction temperature and the reaction time, the reaction temperature is preferably 15° C. or more, more preferably 50° to 95° C. from the viewpoints of the preferable reaction speed and the suppression of the decomposition of the starting material and the formed aminoguanidine and the suppression of the side reactions. The preferable reaction time is about 30 minutes to 8 hours, more preferably 2 to 5 hours.

To the solution of the salt of aminoguanidine obtained in the above reaction, an acid is added and then a nitrite solution is added to allow the reaction therebetween. As a result, a solution of a salt of diazoguanidine is formed, the acids usable in this reaction include, for example, hydrochloric acid, sulfuric acid, nitric acid or other inorganic acids. The use of hydrochloric acid is most preferable from the viewpoints of the reactivity.

There are no specific limitation to the amount of the acid to be used, the preferable amount of the acid is 0.5 to 3 equivalent, more preferably 0.8 to 1.2 equivalent based upon 1 mole of the salt of aminoguanidine.

The nitrites usable in the present invention preferably include sodium nitrite, potassium nitrite, calcium nitrite, ammonium nitrite. From the viewpoints of the reactivity, the use of alkali metal salts of nitrite is preferable and from the viewpoints of solubility and also from the economical viewpoints, the use of sodium nitrite is further preferable. Although there are no specific limitations to the amount of the nitrate, the use of the nitrate in an amount of 0.5 to 3.0 equivalent, more preferably 0.8 to 1.2 equivalent, based upon 1 mole of the salt of aminoguanidine is preferable.

The nitrites are preferably added to the reaction mixture in the form of a solution in the same solvent as used in the previous step or in a solvent missible with the solvent used in the previous step. The preferable concentration of the nitrite in the solution is 5 to 100% by weight.

The reaction is preferably carried out at a reaction temperature of 50° C. or less, more preferably 0° C. to 40° C, from the viewpoints of the reaction velocity. The preferable reaction time is 5 minutes to 5 hours, although this is not critical.

According to the present invention, a pH of the above-prepared reaction solution is preferably adjusted to 1 to 9, more preferably 1 to 3, with the addition of an alkaline solution to the reaction solution. Thereafter the reaction mixture is heated to thereby effect the desired cyclization (or ring forming). Thus, the desired 5-aminotetrazole hydride can be produced in the form of a crystal. The above-mentioned cyclization reaction can be preferably carried out at a pH of 1 to 9, more preferably 1 to 3.

The alkalis usable for the pH adjustment are not specifically limited, but preferably include inorganic alkali such as sodium hydroxide, potassium hydroxide, calcium hydroxide. Although various solvents can be used, the use of an aqueous sodium hydroxide solution is preferable from the viewpoints of the easy reactivity and availability.

The reaction is preferably carried out, while vigorously stirring, by adding an alkaline solution in a concentration of, for example, 5 to 100% by weight in such a rate that the reaction temperature of, preferably, 40°–100° C., more preferably 70°–95° C., can be maintained during the reaction.

Although there are no specific limitations to the reaction time of the cyclization, the reaction time is preferably 15 minutes to 6 hours, more preferably 1 to 3 hours.

After the completion of the reaction, the reaction mixture is preferably gradually cooled to a temperature of, for example, 5° C. or less, to precipitate the desired 5-aminotetrazole hydrate in the crystalline form. The yield of the crystal is usually 70% or more, based upon the starting hydrazine, and the purity is usually 95% or more, determined by a neutralization titration.

Thus, the desired 5-aminotetrazole according to the present invention is obtained in the form of hydrate. If desired, the 5-aminotetrazole having a high purity can be obtained by purifying the above product using, for example, column chromatography, or recrystallization.

The recrystallization can be carried out by using a polar solvent such as water, an alcohol (e.g., methanol, ethanol, isopropanol, n-propanol, etc.), dimethylformamide (DMF), but the use of water is preferable from the viewpoints of the solubility and also from the economical viewpoints. For example, the crystals of 5-aminotetrazole hydrate obtained in the above-mentioned reaction according to the present invention is dissolved, upon heating, in 0.5 to 6 times by weight of a solvent, followed by cooling to crystallize the desired product. The crystallized product is recovered by filtration. The resultant wet crystals are dried under reduced pressure at a temperature of, for example, 30° C. or less, more preferably 20° C. or less, to give the desired 5-aminotetrazole hydrate having a purity of 98% or more in the crystalline form.

The hydrate crystals obtained above can be converted to the anhydrous (or water-free) form by drying a conventional dryer such as a box-type dryer, a fluidized dryer, a flash dryer. Especially, when the anhydrous alkali metal salts (e.g., potassium salt) of 5-aminotetrazole having a large solubility to water is desired to produce, the reaction solution obtained by the reaction in an aqueous solution can be advantageously directly spray dried. This is also preferable from the viewpoints of the yield and simplification of the process steps.

The drying conditions depend upon the type of the dryer to be used. When a box-type dryer is used, the use of the drying temperature of 60° to 200° C., more preferably 80° to 150° C. and the drying time of 30 minutes to 48 hours, more preferably 8 to 16 hours is preferable from the viewpoints of the dewatering velocity and the prevention of decomposition of anhydrous 5-aminotetrazole.

When anhydrous metal salts, especially alkali metal or alkaline earth metal salts are intended to produce, the desired anhydrous product can be directly obtained from the reaction solution by spray drying the uniform solution obtained by neutralizing the 5-aminotetrazole with an equivalent amount of a metal hydroxide or oxide. Thus, the conventional steps for obtaining the anhydrous product by the concentration, separation and drying can be omitted.

In the case of the spray drying, the hot air temperature is set to a temperature higher than those of 10 the conventional box-type dryer, fluidized dryer, and flash dryer, to effect the vaporization of a solvent. Typically, the use of the hot air temperature of 120° to 230° C., more preferably 180° to 215° C. is preferable, provided that the temperature should be not more than the decomposition temperature of the anhydrous product to be dried. The dried product thus obtained is in the form of power, of which specific surface area is larger by several times or more than that obtained by, for example, box drying.

EXAMPLES

The present invention will now be further illustrated by, but is by no means limited to, the following Examples.

Example 1

To a 1000 ml four necked flask provided with a thermometer and an agitating means, 65.0 g (1.3 mole) of hydrazine-monohydrate was charged. While agitating, 131.8 g (1.3 mole) of 36% by weight aqueous hydrochloric acid was added to neutralize and, then, 109.2 g (1.3 mole) of 50% by weight aqueous cyanamide solution and 185 g of water were dropwise added, followed by reacting at 85° C. for 3 hours. After completion of the reaction, 121.6 g of 36% by weight aqueous hydrochloric acid was added to the reaction mixture and at a reaction temperature of 40° C. or less, 321.7 g (1.2 mole) of 26% by weight aqueous sodium nitrite solution was dropwise added. After allowing to stand at room temperature over night, 48.5 g (1.2 mole) of 99% sodium hydroxide was added to allow the reaction mixture to react at a reaction temperature of 85° C. for 3 hours. After completion of the reaction, the reaction mixture was cooled to 3° C. The reaction mixture separated by suction filtration to obtain 124.0 g of 5-aminotetrazole in the crystalline form.

Figure 1:
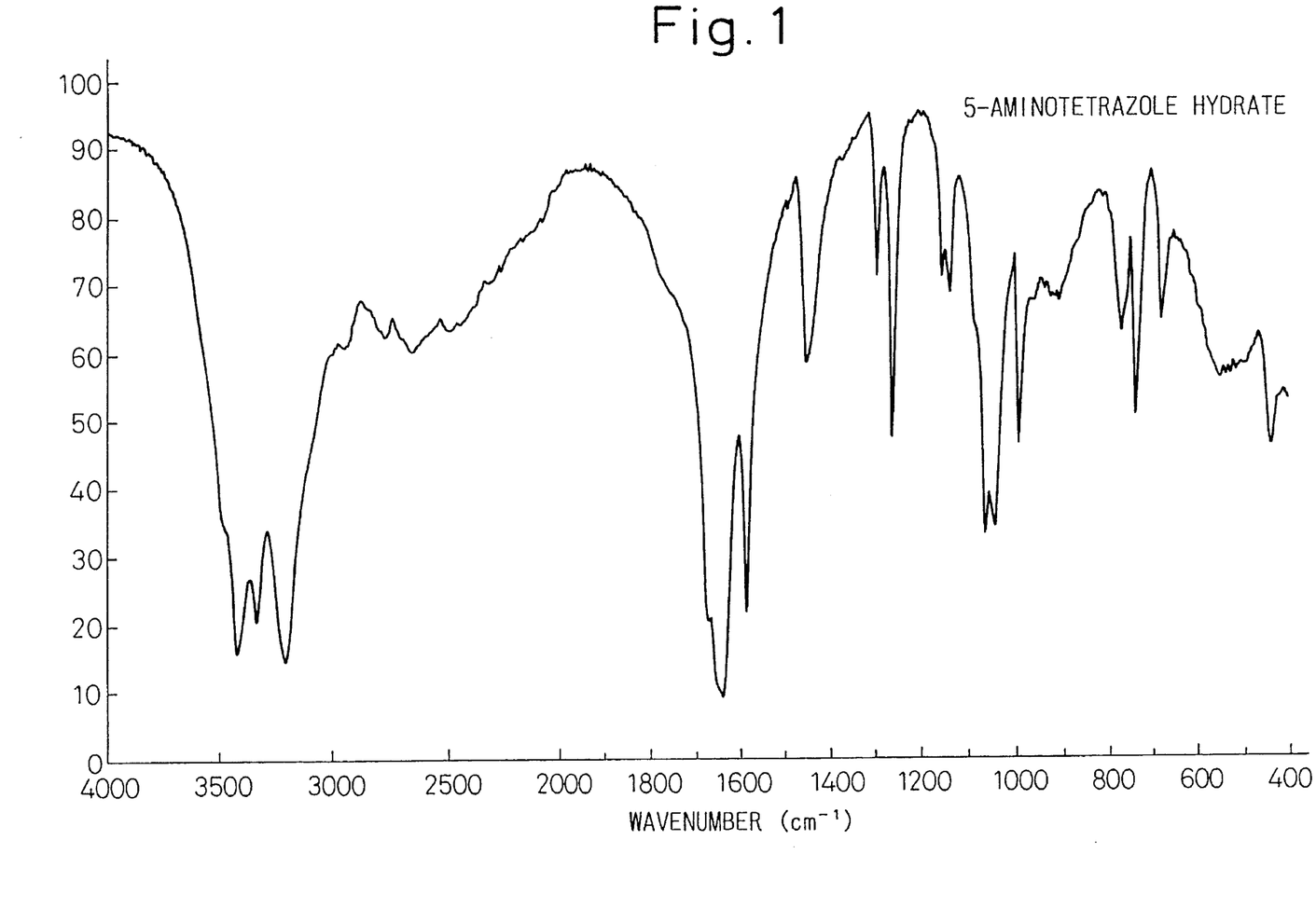
FIG. 1 is an IR spectrum of the desired compound, i.e., 5-aminotetrazole hydrate, obtained by the process according to the present invention.

To the crystalline 5-aminotetrazole obtained above, 372.0 g of water was added, followed by heating until 85° C. to effect the dissolution. The solution was then cooled to 3° C. Thus, by suction filtration, 103.8 g of 5-aminotetrazole hydrate in the wet crystalline form. The wet crystal thus obtained was dried under reduced pressure at room temperature for one hour. Thus, 97.7 g (yield 72.9%) of 5-aminotetrazole (i.e., "AT") monohydrate in the crystalline form having a purity of 99.9% was obtained. The resultant purified 5-aminotetrazole hydrate had a melting temperature of 207°–209° C. and it was observed by a thermogravimetric analysis that the weight corresponding to the monohydrate was decreased before the melting. The result of an IR analysis is shown in FIG. 1 and is the same as that of the standard sample.

Figure 2:
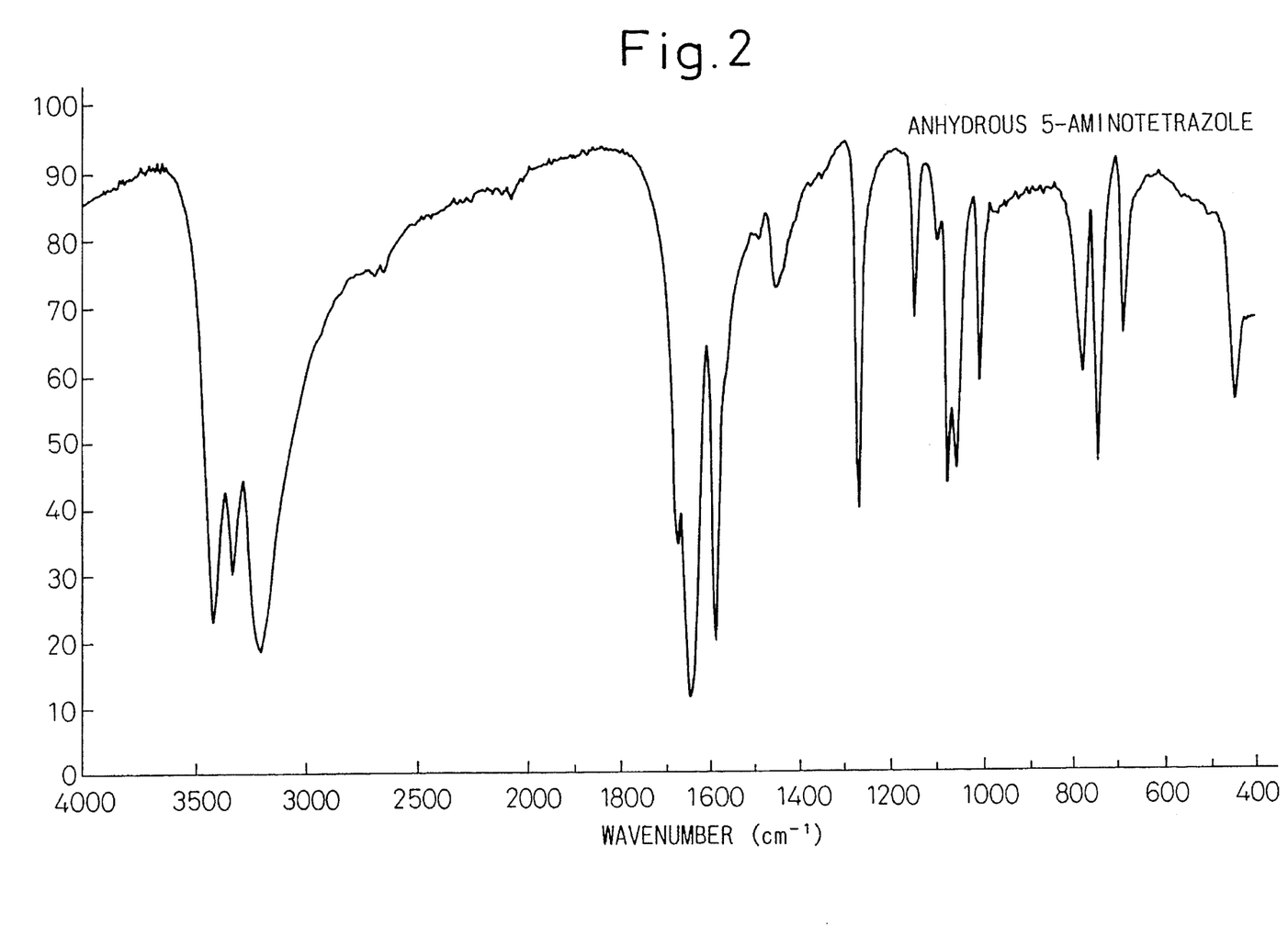
FIG. 2 is an IR spectrum of the desired compound, i.e., anhydrous 5-aminotetrazole, obtained by the process according to the present invention.

A 5.12 g amount of the 5-aminotetrazole hydrate obtained above was spread in a dryer and was heated at 110° C. for 12 hours to remove the water of crystallization. Thus, 4.21 g of the anhydrous 5-aminotetrazole having a purity of 100.0% (yield=99.6% based upon 5-aminotetrazole hydrate). The melting temperature of the resultant anhydrous 5-aminotetrazole was 207°–209° C. and the result of an IR analysis is shown in FIG. 2 and is the same as that of the standard sample.

Example 2

To the apparatus similar to Example 1, 129.5 g (1.0 mole) of hydrazine.½ sulfate and 25 g of water were charged and 84.0 g of 50% aqueous cyanamide solution was dropwise added, followed by reacting at 85° C. for 3 hours. After completion of the reaction, 127.3 g (0.5 mole) of 35% sulfuric acid was added and, in the similar manner as in Example 1, 73.3 g (0.71 mole) of 5-aminotetrazole hydrate in the crystalline form was obtained (yield=71.2% based upon hydrazine sulfate). The resultant 5-aminotetrazole hydrate had a melting temperature of 207°–209° C. and the decrease in the weight corresponding to the weight of the monohydrate was observed before the melting by a thermogravimetric analysis. Furthermore, the result of an IR analysis is the same as that of FIG. 1 and is the same as that of the standard sample.

Example 3

Example 1 was repeated, except that crystalline cyanamide (purity=98%) was used instead of 50% aqueous cyanamide solution. As a result, 97.1 g (0.94 mole) of 5-aminotetrazole hydrate in the crystalline form was obtained (yield=72.3% based upon hydrazine sulfate). The resultant 5-aminotetrazole hydrate had a melting temperature of 207°–209° C. and the decrease in the weight corresponding to the weight of the monohydrate was observed before the melting by a thermogravimetric analysis. Furthermore, the result of an IR analysis is the same as that of FIG. 1 and is the same as that of the standard sample.

Example 4

To a 100 liter solution vessel provided with a thermometer and an agitating means, 51.045 kg of distilled water was charged. While agitating, 0.515 kg (6.00 mole) of 5-aminotetrazole in the form of powder was dissolved. Thus, 51.560 kg of 1% by weight aqueous 5-aminotetrazole solution was obtained.

The aqueous solution obtained above was charged, by a continuous flow pump, to a spray dryer (i.e., OUT-12 available from Ohkawara Kakohki K. K., Japan). The pressurized nozzle was used as a spray nozzle. The apparatus was composed of a drying chamber and cyclone and finely divided powder was collected in a stainless steel collection bottle provided at the bottom of the drying chamber and cyclone.

The hot air temperature of the spray dryer was set to 215° C. After the hot air temperature reached the setting temperature, the above aqueous solution was introduced to the spray dryer at a flow rate of 15 liter/hr. It was confirmed from the observation window that the dry crystal was obtained immediately after the introduction.

After completion of the introduction of the aqueous solution, a heater for the hot air was turned off. After allowing the apparatus to cool, the sample was collected. The powder sample obtained from the sample collection bottle and the drying chamber was 0.390 kg. The water content of the sample thus obtained was 0.10% by weight, determined by a Karl Fisher method. Thus, it was confirmed that the anhydrous product was obtained. The yield from the aqueous solution was thus 75%. Furthermore, according to a scanning type electro micrograph, it was confirmed that the resultant powdery crystals were substantially spheric and granular type particles. The particle size distribution was determined by a laser diffraction type particle size distribution meter (i.e., Microtrac FRA available from Leed's & Northrup Co., U.S.A.). When the particle size distribution was determined using n-heptane as a dispersion medium, the cumulative 10% diameter was 12 μm, the cumulative 50% diameter was 27 μm, the cumulative 90% diameter was 49 μm and the average diameter was 30 μm, all based upon the volume diameter.

After spray drying test, the drying chamber was washed with about 6 liters of water and the washed solution was concentrated and dried to solid. The resultant solid was 0.258 kg, which contained 99.8% by weight of 5-aminotetrazole and 0.2% by weight of water, as a result of the analysis. Thus, the resultant solid was the anhydrous product. This anhydrous product corresponded to 20% by weight of the starting material dissolved in the distilled water and the recovered anhydrous product has the sufficient quality to be commercially used.

Example 5

To a 1000 ml four necked flask provided with a thermometer and an agitating means, 482.4 g (3.00 mole) of 35% by weight aqueous potassium hydroxide solution was charged and heated to 80° C. While agitating, 257.8 g (3.00 mole) of 5-aminotetrazole in the form of powder was added. Thus, 739.0 g of 50% by weight aqueous potassium salt of 5-aminotetrazole solution was obtained, after reacting for 30 minutes.

The aqueous solution obtained above was charged, by a continuous flow pump, to a spray dryer (i.e., Mobile Minor available from Niro Co., Denmark). The rotary disc nozzle was used as a spray nozzle. The apparatus was composed of a drying chamber and cyclone and finely divided powder was collected in a stainless steel collection bottle provided at the bottom of the cyclone.

The hot air temperature of the spray dryer was set to 200° C. After the hot air temperature reached the setting temperature, the above aqueous solution was introduced to the spray dryer at a flow rate of 600 ml/hr. It was confirmed from the observation window that the dry crystal was obtained immediately after the introduction.

After completion of the introduction of the aqueous solution, a heater for the hot air was turned off. After allowing the apparatus to cool, the sample was collected. The powder sample obtained from the sample collection bottle and the drying chamber was 277.1 g. The water content of the sample thus obtained was 0.03% by weight, determined by a Karl Fisher method. Thus, it was confirmed that the anhydrous product was obtained. The yield from the aqueous solution was thus 75%. Furthermore, according to a scanning type electro micrograph, it was confirmed that about 50% of the resultant powdery crystals were substantially spheric type particles. The particle size distribution was determined by a laser diffraction type particle size distribution meter (i.e., Microtrac FRA available from Leed's & Northrup Co., U.S.A.). When the particle size distribution was determined using n-heptane as a dispersion medium, the cumulative 10% diameter was 7 μm, the cumulative 50% diameter was 26 μm, the cumulative 90% diameter was 46 μm and the average diameter was 27 μm, all based upon the volume diameter.

Figure 3:
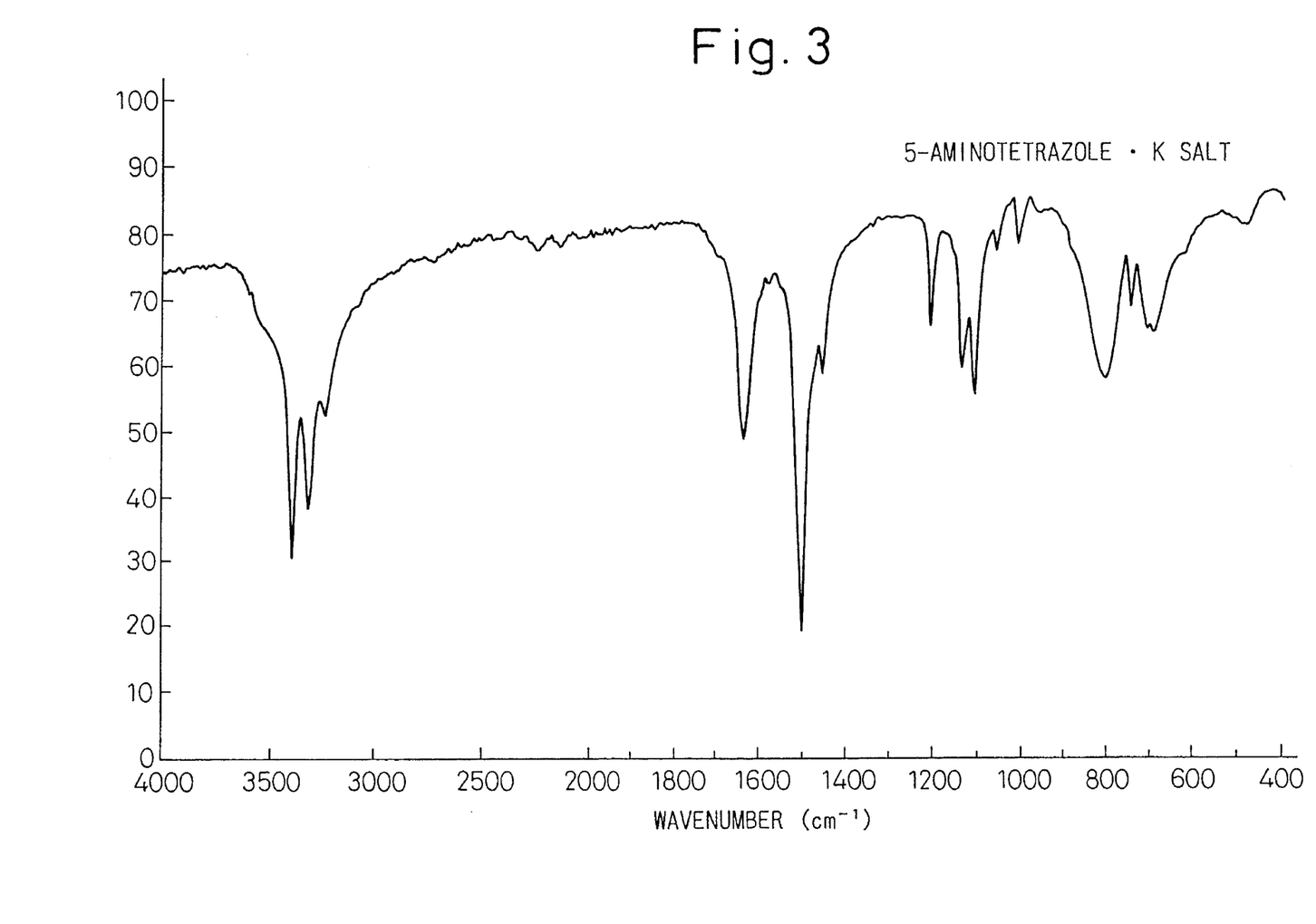
FIG. 3 is an IR spectrum of the desired compound, i.e., the potassium salt of 5-aminotetrazole, obtained by the process according to the present invention.

After spray drying test, the drying chamber was washed with about 3 liters of water and the washed solution was concentrated and dried to solid. The resultant solid was 74.0 g, which contained 99.8% by weight of potassium salt of 5-aminotetrazole and 0.2% by weight of water, as a result of the analysis. Thus, the resultant solid was the anhydrous product. This anhydrous product corresponded to 20% by weight of the starting potassium salt and the recovered anhydrous product has the sufficient quality to be commercially used. Futhermore, the result of an IR analysis is shown in FIG. 3 and is the same as that of the standard sample.

Example 6

To a 2000 ml four necked flask provided with a thermometer and an agitating means, 76.5 g (0.90 mole) of 5-aminotetrazole and 1000 g of water was charged and heated to 80° C. Thereafter, 363.2 g (0.45 mole) of 5% by weight of magnesium oxide slurry was dropwise added, followed by allowing to react for one hour. While agitating, thus 1438.0 g of 6% by weight aqueous magnesium salt of 5-aminotetrazole solution was obtained.

The aqueous solution obtained above was charged, to a spray dryer in the same manner as in Example 4, except that the sample solution to be introduced was different. The spray drying conditions were the same as in Example 4. It was confirmed from the observation window that the dry crystal was obtained immediately after the introduction.

After completion of the introduction of the aqueous solution, a heater for the hot air was turned off. After allowing the apparatus to cool, the sample was collected. The powder sample obtained from the sample collection bottle and the drying chamber was 65.0 g. The water content of the sample thus obtained was 0.10% by weight, determined by a Karl Fisher method. Thus, it was confirmed that the anhydrous product was obtained. The yield from the aqueous solution was thus 75%. Furthermore, according to a scanning type electro micrograph, it was confirmed that the substantial amount of the resultant powdery crystals were nearly spheric type particles. The particle size distribution was determined in the same manner as in Example 4. When the particle size distribution was determined in the same manner as in Example 4, the cumulative 10% diameter was 6 μm, the cumulative 50% diameter was 18 μm, the cumulative 90% diameter was 44 μm and the average diameter was 30 μm, all based upon the volume diameter.

Figure 4:
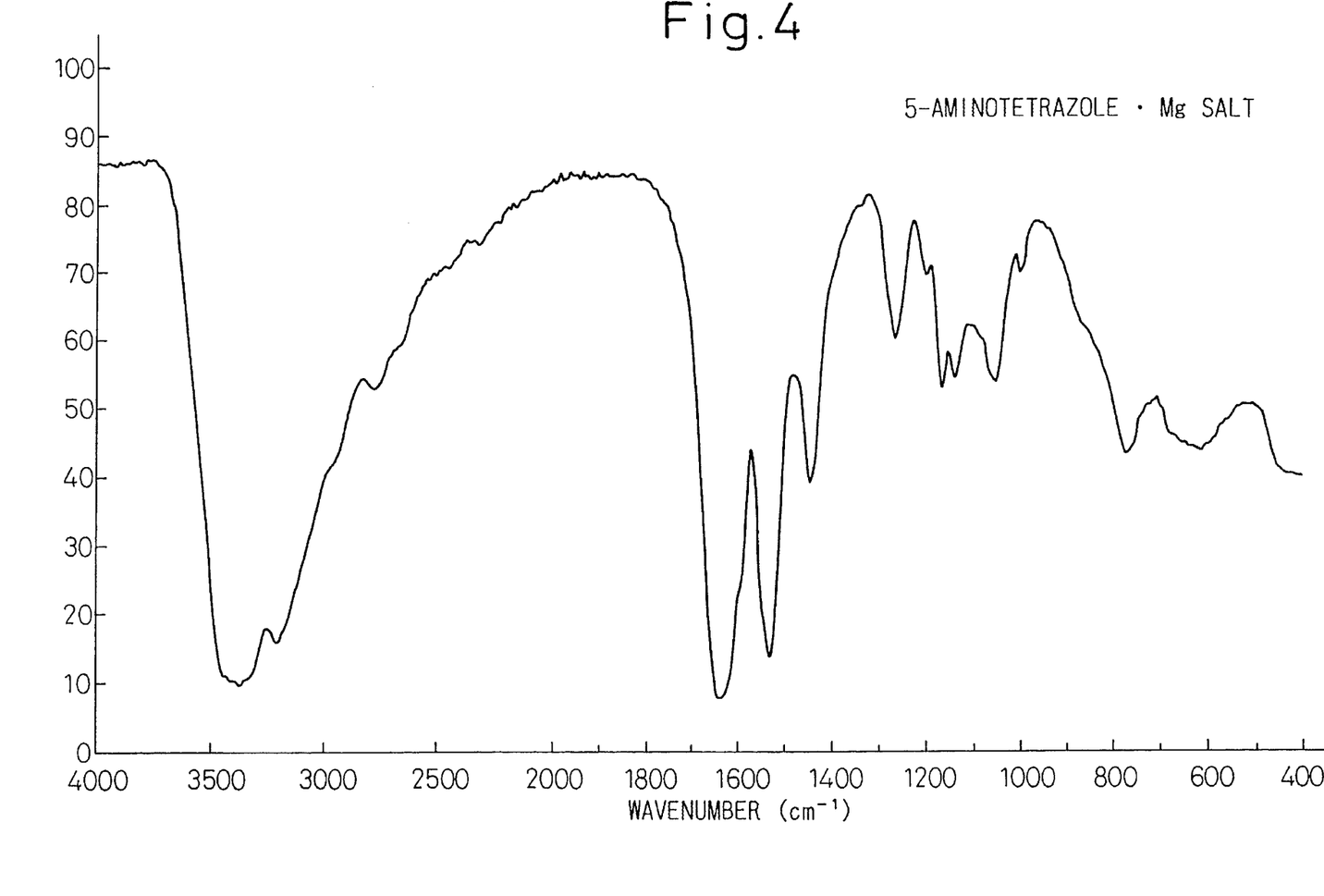
FIG. 4 is an IR spectrum of the desired compound, i.e., the magnesium salt of 5-aminotetrazole, obtained by the process according to the present invention.

After spray drying test, the drying chamber was washed with about 3 liters of water and the washed solution was concentrated and dried to solid. The resultant solid was 17.3 g, which contained 99.8% by weight of magnesium salt of 5-aminotetrazole and 0.2% by weight of water, as a result of the analysis. Thus, the resultant solid was the anhydrous product. This anhydrous product corresponded to 20% by weight of the starting magnesium salt and the recovered anhydrous product has the sufficient quality to be commercially used. Furthermore, the result of an IR analysis is shown in FIG. 4 and is the same as that of the standard sample.

Comparative Example 1

To a 1000 ml four necked flask provided with a thermometer and an agitating means, 103.0 g (1.20 mole) of 5-aminotetrazole and 300.0 g of methanol were charged. 5-aminotetrazole and 300.0 g of methanol were charged. While agitating, 379.2 g (0.60 mole) of 21% by weight solution of potassium hydroxide in methanol was dropwise added, followed by allowing to react at 25° C. for 30 minutes. After completion of the reaction, the reaction mixture was concentrated at a temperature of 67° C. After distilling off 301 g of μmethanol, the reaction mixture was cooled to 20° C. and the reaction mixture was separated by a suction filtration. Thus, 112.2 g of the wet crystal was obtained. The wet crystal thus obtained was dried at 80° C. for 12 hours to obtain 100.1 g (yield=67.3%) of potassium salt of 5-aminotetrazole in the crystalline form having a purity of 99.5%. The resultant purified potassium salt of 5-aminotetrazole had a melting temperature of 267°–269° C. The result of the quantitative determination of potassium according to an inductive coupling type plasma analysis (ICP) was 31.3%, which substantially corresponds to the potassium content of a 1:1 composition of 5-aminotetrazole and potassium.

Comparative Example 2

To a 1000 ml four necked flask provided with a thermometer and an agitating means, 76.5 g (0.90 mole) of 5-aminotetrazole and 450.0 g of water were charged. While agitating, 360.0 g (0.90 mole) of 16.5% by weight aqueous potassium hydroxide solution was dropwise added, followed by allowing to react at 25° C. for 30 minutes. After completion of the reaction, the resultant reaction mixture was concentrated in an evaporator. After 752.3 g of water was distilled off, the resultant mixture was cooled to 20° C. The suction filtration was tried to separate the solid product, but the filtering properties were very poor. Therefore, the concentration was continued to effect in the evaporator. Finally, the mixture was solid dried. The crystals adhered to the walls of the evaporator vessel were seratched off and powdered to obtain 129.0 g of the wet crystals. The wet (yield 96.2%) of the potassium salt of 5-aminotetrazole in the crystalline form having a purity of 99.2%.

The physical properties of the products obtained in Examples 1, 4–6 and Comparative Example 1 are shown in Table 1. The determination methods are as follows.

Heat of Decomposition

According to a JIS (Japan Industrial Standards) M8813 method "Coals and Cokes-Method for Determining Heat of Calorific Power" determined by Nenban-shiki Type B calorimeter Decomposition Initiatinq Temperature The exothermic initiating temperature of a differential scanning calorimeter Combustion Test 1. A test sample was prepared by mixing 30 parts by weight of a sample to be tested with 70 parts by weight of an oxygen source (i.e., potassium nitrate).

2. The test sample was formed to a shape having a length of 250 mm, a width of 20 mm and a height of 10 mm, based upon a test method for a flammable solid (4.1) in the so-called "Orange Book".
3. One edge of the test sample was heated by a gas burner and the combustion conditions and the exposure conditions were observed.

The results are shown in the following Table 1.

TABLE 1

| No. | Sample | Drying method | Shape of cyrstalline (SEM) | Purity (%) | Particle size distribution/Microtrac FRA (μm) | | | | Specific surface area/BET ($m^2/g$) | Heat of decomposition (cal/g) | Decomposition initiating temp. (°C.) | Combustion test |
| --- | --- | --- | --- | --- | --- | --- | --- | --- | --- | --- | --- | --- |
| | | | | | 10% diameter | 50% diameter | 90% diameter | Average diameter | | | | |
| Example 1 | anhydrous 5AT | Crystallization Box drying | Needle | 99.2 | 55.6 | 199.7 | 472.5 | 238.2 | 0.12 | 2860 | 219 | Decomposition No exposure |
| Example 4 | anhydrous 5AT | Spray drying | Powder particle | 98.8 | 12.2 | 27.4 | 49.0 | 29.9 | 0.70 | 2850 | 218 | Decomposition No exposure |
| Comp. Ex. 1 | 5AT K salt | Crystalline Box drying | Rectangular | 99.5 | 56.2 | 110.3 | 193.4 | 119.8 | 0.09 | 2060 | 315 | Decomposition after melting No exposure |
| Example 5 | 5AT K salt | Spray drying | Nearly sphere | 98.2 | 7.1 | 25.8 | 46.2 | 27.0 | 0.68 | 2050 | 313 | Decomposition after melting No exposure |
| Example 6 | 5AT Mg salt | Spray drying | Nearly sphere | 98.4 | 6.4 | 18.0 | 43.6 | 30.0 | 0.72 | 1960 | 220 | Decomposition after melting No exposure |

As is clear from the above explanation, the present process relates to a production of 5-aminotetrazole, without isolating the intermediate, at a high yield, which is conventionally produced by the steps of isolating and purifying the intermediates, i.e., aminoguanidine and salts of diazoguanidine from cyanamide and hydrazine.

According to the present process, the various problems passesed by the known processes, e.g., danger of the intermediates and the increase in the production cost caused therefrom and insufficient yield, can be solved and the desired compounds, 5-aminotetrazole hydrate and anhydrous 5-aminotetrazole can be produced with safety and less expensive costs in a commercial scale.

Furthermore, according to the present invention, finely divided alkali metal salts of 5-aminotetrazole, which is capable of uniformly mixing and dispersing with fuels, oxidants and additives, can be advantageously by using a spray drying as a drying method.

We claim:

1. A process for producing 5-aminotetrazole comprising the steps of:
   (a) reacting cyanamide with hydrazine in a solvent to form a salt of aminoguanidine;
   (b) adding thereto an acid and then a nitrite to form a salt of diazoguanidine; and
   (c) cyclizing the salt of diazoguanidine, upon heating, to thereby produce the 5-aminotetrazole, without isolating the intermediate product.

2. A process as claimed in claim 1, wherein 0.8 to mole, based upon 1 mole of the hydrazine, of cyanamide is reacted with the hydrazine in the step (a).

3. A process as claimed in claim 1, wherein 0.5 to equivalent of the acid and 0.5 to 3 equivalent of the nitrite, both based upon 1 mole of the aminoguanidine are used in the step (b).

4. A process as claimed in claim 1, wherein the cyclization is carried out at a pH of 1 to 9.

5. A process for producing 5-aminotetrazole or a metal salt thereof in the form of powder comprising spray drying a solution of the 5-aminotetrazole obtained by the method of claim 1 or a metal salt thereof.

* * * * *